United States Patent
Nomura et al.

(10) Patent No.: US 8,703,899 B2
(45) Date of Patent: Apr. 22, 2014

(54) METHOD FOR PRODUCING POLYESTER, AND FLUORINE-CONTAINING DICARBOXYLIC ACID ESTER COMPOUND

(71) Applicant: Asahi Glass Company, Limited, Tokyo (JP)

(72) Inventors: Jumpei Nomura, Tokyo (JP); Hidekazu Okamoto, Tokyo (JP); Atsushi Fujimori, Tokyo (JP); Takashi Okazoe, Tokyo (JP)

(73) Assignee: Asashi Glass Company Limited, Tokyo (JP)

( * ) Notice: Subject to any disclaimer, the term of this patent is extended or adjusted under 35 U.S.C. 154(b) by 0 days.

(21) Appl. No.: 14/014,977

(22) Filed: Aug. 30, 2013

(65) Prior Publication Data
US 2013/0345387 A1    Dec. 26, 2013

Related U.S. Application Data

(63) Continuation of application No. PCT/JP2012/054957, filed on Feb. 28, 2012.

(30) Foreign Application Priority Data

Mar. 2, 2011  (JP) .................. 2011-045195

(51) Int. Cl.
C08G 63/02    (2006.01)
C08G 63/00    (2006.01)

(52) U.S. Cl.
USPC ........... 528/191; 528/176; 528/190; 528/193; 528/194; 528/196

(58) Field of Classification Search
USPC ............... 264/176.1; 528/176, 190, 191, 193, 528/194, 196
See application file for complete search history.

(56) References Cited

U.S. PATENT DOCUMENTS 4,966,958 A    10/1990    Tacke et al.

FOREIGN PATENT DOCUMENTS

| GB | 924607 | 4/1963 |
|---|---|---|
| JP | B1-38-15247 | 8/1963 |
| JP | A-S53-114895 | 10/1978 |
| JP | A-S57-149327 | 9/1982 |
| JP | A-H02-67315 | 3/1990 |
| JP | A-H8-231698 | 9/1996 |
| JP | A-H8-231699 | 9/1996 |
| JP | B-3522031 | 4/2004 |
| JP | B-3552820 | 5/2004 |

OTHER PUBLICATIONS

International Search Report for Application No. PCT/JP2012/054957 dated May 29, 2012.
Mahajan et al., "Aromatic Polyesters via Transesterification of Dimethylterephthalate/Isophthalate with Bisphenol-A," Journal of Applied Polymer Science, vol. 61, No. 13, 1996, pp. 2297-2304.
Oishi et al., "Model Studies and a New Melt Polycondensation Route to Poly-Bisphenol Also/terephthalate (Polyarylate)," Journal of Polymer Science: Part A: Polymer Chemistry, vol. 30, 1992, pp. 83-89.
Park et al., "Chemoenzymatic Synthesis of Sucrose-Containing Aromatic Polymers," Biotechnology and Bioengineering, vol. 72, No. 5, 2001, pp. 541-547.
Van der Schuur et al., "Synthesis of polyether-based block copolymers based on poly(propylene oxide) and terephthalates," Polymer, vol. 46, 2005, pp. 327-333.

*Primary Examiner* — Terressa Boykin
(74) *Attorney, Agent, or Firm* — Foley & Lardner LLP

(57) ABSTRACT

The present invention relates to a method for producing a polyester, containing conducting a transesterification reaction of at least one compound selected from compounds represented by the following formulae (1) to (3) with a diol compound in the presence of a catalyst:

[Chem. 1]

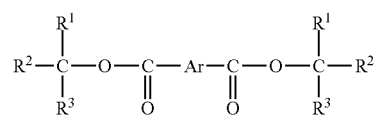

(1)

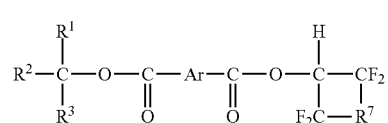

(2)

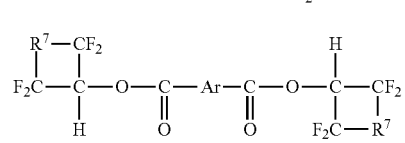

(3)

wherein Ar is a divalent aromatic hydrocarbon group or the like; $R^1$ is $CX^1Y^1R^4$; $R^2$ is a hydrogen atom or $CX^2Y^2R^5$; $R^3$ is a hydrogen atom or $CX^3Y^3R^6$; $R^7$ is a perfluoroalkylene group having 1 to 5 carbon atoms; $X^1$ to $X^3$ are a hydrogen atom, a fluorine atom or $R^f$; $Y^1$ to $Y^3$ are a fluorine atom or $R^f$; $R^4$ to $R^6$ are a fluorine atom, $R^f$, $OR^f$ or the like; and $R^f$ is a fluoroalkyl group having 1 to 4 carbon atoms.

11 Claims, No Drawings

METHOD FOR PRODUCING POLYESTER, AND FLUORINE-CONTAINING DICARBOXYLIC ACID ESTER COMPOUND

TECHNICAL FIELD

The present invention relates to a method for producing a polyester, and a fluorine-containing dicarboxylic acid ester compound.

BACKGROUND ART

Polyesters have been used for various purposes such as fibers, films and containers, because of their excellent mechanical properties and moldability. In particular, polyarylates which are polycondensates of aromatic dicarboxylic acids and aromatic diols exhibit various excellent properties (such as heat resistance, flame retardance, impact resistance, bending recovery properties, UV barrier properties, chemical resistance and electric properties), in addition to the mechanical properties and moldability, so that they have been widely used as engineering plastics in many industrial fields.

As methods for producing polyarylates, there have been known, for example, the following methods:

(i) An interfacial polycondensation method of an alkali metal salt or alkali earth metal salt of an aromatic diol compound with a dicarboxylic acid dichloride, (ii) An acetic acid elimination polycondensation method (melt polycondensation method) of a diacetate of an aromatic diol compound with a dicarboxylic acid, and (iii) A phenol elimination polycondensation method (melt polycondensation method) of a diphenyl ester of a dicarboxylic acid with an aromatic diol compound.

However, the method of (i) has problems that the expensive dicarboxylic acid dichloride is used as a raw material, that a solvent such as methylene chloride is used in large amounts, that it is necessary to wash and remove a salt generated in the reaction, that impurities such as a solvent remain in the polyarylate, and the like.

In the methods of (ii) and (iii), raw materials can be synthesized from various dicarboxylic acid derivatives, but the reaction is performed at high temperature. Therefore, coloration is liable to occur due to the influence of oxygen and the like. Further, the melt viscosity of the reaction system becomes extremely high at the late stage of the reaction, so that it becomes difficult to efficiently draw out reaction by-products (such as water, monocarboxylic acids and phenols) to the outside of the reaction system. Accordingly, the polycondensation reaction for increasing the molecular weight to a desired value is required to be performed at high temperature for a long period of time. Furthermore, if the monocarboxylic acids or the phenols remain in the polyarylate, they cause coloration or strength reduction of the polyarylate.

As methods for drawing the monocarboxylic acids or the phenols out of the polyarylate of a high-viscosity state in the melt polycondensation method, there have been proposed, for example, the following methods:

(iv) A method of continuously reacting a diphenyl ester of a dicarboxylic acid with an aromatic diol compound by using a combination of a wiped film reactor and a twin-screw horizontal extruder having 5 exhaust outlets (see Patent Document 1), (v) A method of polymerizing a polyarylate prepolymer in a molten state while allowing it to freely drop from a perforated plate (see Patent Document 2), and (vi) A method of polymerizing a polyarylate prepolymer in a molten state while allowing it to drop along a guide from a perforated plate (see Patent Document 3).

However, the methods of (iv) to (vi) also have a problem that the temperature of the polycondensation reaction must be set high, in order to draw out the phenols having a high boiling point to the outside of the polymerization system.

PRIOR-ART DOCUMENTS

Patent Documents

Patent Document 1: JP-A-57-149327
Patent Document 2: Japanese Patent No. 3552820
Patent Document 3: Japanese Patent No. 3522031

SUMMARY OF THE INVENTION

Problems that the Invention is to Solve

The present invention provides a method which can produce a polyester having little coloration, a high purity and a high molecular weight.

Means for Solving the Problems

The method for producing a polyester according to the present invention, comprising conducting a transesterification reaction of at least one compound selected from the group consisting of a compound represented by the following formula (1), a compound represented by the following formula (2) and a compound represented by the following formula (3) with a diol compound in the presence of a catalyst.

[Chem. 1]

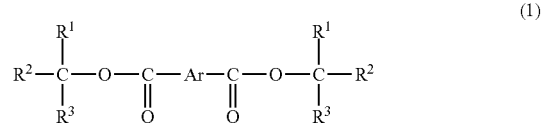
(1)

In the formula, Ar is a divalent aromatic hydrocarbon group or a divalent aromatic heterocyclic group, $R^1$ is a group represented by $CX^1Y^1R^4$, and two $R^1$s may be the same or different from each other, $R^2$ is a hydrogen atom or a group represented by $CX^2Y^2R^5$, and two $R^2$s may be the same or different from each other, $R^3$ is a hydrogen atom or a group represented by $CX^3Y^3R^6$, and two $R^3$s may be the same or different from each other, $X^1$ to $X^3$ are each independently a hydrogen atom, a fluorine atom or $R^f$, $Y^1$ to $Y^3$ are each independently a fluorine atom or $R^f$, $R^4$ to $R^6$ are each independently a fluorine atom, $R^f$, $OR^f$ or an alkyl group having 1 to 6 carbon atoms, and $R^f$ is independently a fluoroalkyl group (which may contain an etheric oxygen) having 1 to 4 carbon atoms.

[Chem. 2]

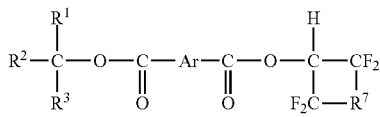
(2)

In the formula, Ar is a divalent aromatic hydrocarbon group or a divalent aromatic heterocyclic group,
$R^1$ is a group represented by $CX^1Y^1R^4$,
$R^2$ is a hydrogen atom or a group represented by $CX^2Y^2R^5$,
$R^3$ is a hydrogen atom or a group represented by $CX^3Y^3R^6$,
$R^7$ is a perfluoroalkylene group (which may contain an etheric oxygen) having 1 to 5 carbon atoms,
$X^1$ to $X^3$ are each independently a hydrogen atom, a fluorine atom or $R^f$,
$Y^1$ to $Y^3$ are each independently a fluorine atom or $R^f$,
$R^4$ to $R^6$ are each independently a fluorine atom, $R^f$, $OR^f$ or an alkyl group having 1 to 6 carbon atoms, and
$R^f$ is independently a fluoroalkyl group (which may contain an etheric oxygen) having 1 to 4 carbon atoms.

[Chem. 3]

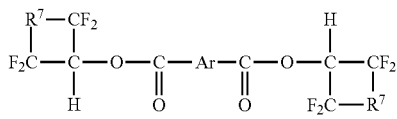
(3)

In the formula, Ar is a divalent aromatic hydrocarbon group or a divalent aromatic heterocyclic group, and
$R^7$ is a perfluoroalkylene group (which may contain an etheric oxygen) having 1 to 5 carbon atoms, and two $R^7$s may be the same or different from each other.

The compound represented by the above formula (1) to (3) is preferably obtained by a reaction using as a starting material at least one fluorine-containing alcohol selected from the group consisting of a compound represented by the following formula (5) and a compound represented by the following formula (6)

[Chem. 4]

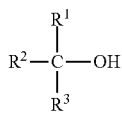
(5)

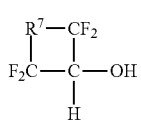
(6)

In the formula, $R^1$ is a group represented by $CX^1Y^1R^4$,
$R^2$ is a hydrogen atom or a group represented by $CX^2Y^2R^5$,
$R^3$ is a hydrogen atom or a group represented by $CX^3Y^3R^6$,
$R^7$ is a perfluoroalkylene group (which may contain an etheric oxygen) having 1 to 5 carbon atoms, $X^1$ to $X^3$ are each independently a hydrogen atom, a fluorine atom or $R^f$,
$Y^1$ to $Y^3$ are each independently a fluorine atom or $R^f$,
$R^4$ to $R^6$ are each independently a fluorine atom, $R^f$, $OR^f$ or an alkyl group having 1 to 6 carbon atoms, and
$R^f$ is independently a fluoroalkyl group (which may contain an etheric oxygen) having 1 to 4 carbon atoms.

The fluorine-containing alcohol preferably has 2 to 10 carbon atoms.
$R^2$ in formula (5) is preferably a group represented by $CX^2Y^2R^5$.
The fluorine-containing alcohol preferably has a pKa of less than 15.
The fluorine-containing alcohol preferably has a pKa of less than 13.
The fluorine-containing alcohol is preferably at least one selected from the group consisting of 2,2,2-trifluoroethanol, 2,2,3,3-tetrafluoro-1-propanol, 2,2,3,3,3-pentafluoro-1-propanol, 1,1,1,3,3,3-hexafluoro-2-propanol, 2-fluoro-1-propanol, 2,2,3,4,4,4-hexafluoro-1-butanol, 2,2,3,3,4,4,5,5-octafluoro-1-pentanol, 2,2,3,3,4,4,5,5-octafluorocyclopentanol, perfluoro(t-butyl)alcohol, and 2,2,3,3,4,4,5,5,6,6-decafluorocyclohexanol.

The diol compound is preferably an aromatic diol compound.
The diol compound is preferably bisphenol A.
The catalyst is preferably an alkali metal salt or an alkali earth metal salt.
The fluorine-containing dicarboxylic acid ester compound according to the present invention is bis(2,2,3,3-tetrafluoropropyl)isophthalate represented by the following formula (1-1).

[Chem. 5]

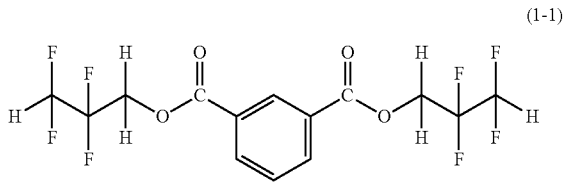
(1-1)

Effects of the Invention

According to the method for producing a polyester of the present invention, there can be produced a polyester having little coloration, a high purity and a high molecular weight.

MODE FOR CARRYING OUT THE INVENTION

In this specification, the compound represented by formula (1) is referred to as compound (1). The compounds represented by the other formulas are also similarly referred.
<Method for Producing Polyester>
The method for producing a polyester of the present invention is a method of obtaining a polyester by conducting a transesterification reaction of the specific fluorine-containing dicarboxylic acid ester compound with a diol compound in the presence of a catalyst.

(Catalysts)

As the catalysts, known transesterification reaction catalysts can be mentioned. Specific examples of the catalysts include carbonates of alkali metals or alkali earth metals (such as sodium carbonate, sodium hydrogen carbonate, potassium carbonate and calcium carbonate), hydroxides of alkali metals or alkali earth metals (such as lithium hydroxide, sodium hydroxide, potassium hydroxide and calcium hydroxide), alkali metal salts, alkali earth metal salts or quaternary ammonium salts of hydrides of boron or aluminum (such as lithium aluminohydride, sodium borohydride, potassium borohydride and tetramethyl ammonium borohydride), hydrides of alkali metals or alkali earth metals (such as lithium hydride, sodium hydride and calcium hydride), alkoxides of alkali metals or alkali earth metals (such as lithium methoxide, sodium ethoxide and calcium methoxide), aryloxides of alkali metals or alkali earth metals (such as lithium phenoxide, sodium phenoxide, magnesium phenoxide, LiO—$Ar^1$—OLi, NaO—$Ar^1$—ONa (wherein $Ar^1$ is an arylene group)), organic acid salts of alkali metals or alkali earth metals (such as lithium acetate, calcium acetate and sodium benzoate), zinc compounds (such as zinc oxide, zinc acetate and zinc phenoxide), boron compounds (such as boron oxide, boric acid, sodium borate, trimethyl borate, tributyl borate and triphenyl borate), silicon compounds (such as silicon oxide, sodium silicate, tetraalkylsilicon, tetraarylsilicon and diphenyl-ethyl-ethoxysilicon), germanium compounds (such as germanium oxide, germanium tetrachloride, germanium ethoxide and germanium phenoxide), tin compounds (such as tin oxide, dialkyltin oxide, dialkyltin carboxylate, tin acetate, tin compounds having an alkoxy group or aryloxy group bonded to tin, such as ethyltin tributoxide, and organotin compounds), lead compounds (such as lead oxide, lead acetate, lead carbonate, basic lead carbonate, and alkoxides or aryloxides of lead or organolead), onium compounds (such as quaternary ammonium salts, quaternary phosphonium salts and quaternary arsonium salts), antimony compounds (such as antimony oxide and antimony acetate), manganese compounds (such as manganese acetate, manganese carbonate and manganese borate), titanium compounds (such as titanium oxide and alkoxides or aryloxides of titanium) and zirconium compounds (such as zirconium acetate, zirconium oxide, alkoxides or aryloxides of zirconium and zirconium acetylacetone).

As the catalysts, the alkali metal salts or alkali earth metal salts (carbonates, hydroxides, salts of hydrides of boron or aluminum, hydrides, alkoxides, aryloxides and organic acid salts) are preferred in view of heat resistance, weather resistance and coloration resistance of the polyester, and the carbonates, hydroxides and salts of hydrides of boron or aluminum of the alkali metals or alkali earth metals are more preferred in view of easy availability and relative inexpensiveness.

The catalysts may be used either alone or in combination of two or more thereof.

The amount of the catalyst used is usually from $10^{-8}$ to 1% by mass, and preferably from $10^{-7}$ to $10^{-1}$% by mass, based on the diol compound of a raw material, in view of polymerization rate (productivity) and deterioration of physical properties of the polyester due to remaining of the catalyst therein.

(Fluorine-Containing Dicarboxylic Acid Ester Compounds)

The fluorine-containing dicarboxylic acid ester compound is at least one selected from the group consisting of compound (1), compound (2) and compound (3).

[Chem. 6]

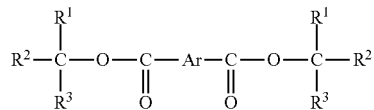

(1)

In the formula, Ar is a divalent aromatic hydrocarbon group or a divalent aromatic heterocyclic group; $R^1$ is a group represented by $CX^1Y^1R^4$, and two $R^1$s may be the same or different from each other; $R^2$ is a hydrogen atom or a group represented by $CX^2Y^2R^5$, and two $R^2$s may be the same or different from each other; $R^3$ is a hydrogen atom or a group represented by $CX^3Y^3R^6$, and two $R^3$s may be the same or different from each other; $X^1$ to $X^3$ are each independently a hydrogen atom, a fluorine atom or $R^f$; $Y^1$ to $Y^3$ are each independently a fluorine atom or $R^f$; $R^4$ to $R^6$ are each independently a fluorine atom, $R^f$, $OR^f$ or an alkyl group having 1 to 6 carbon atoms; and $R^f$ is independently a fluoroalkyl group (which may contain an etheric oxygen) having 1 to 4 carbon atoms.

[Chem. 7]

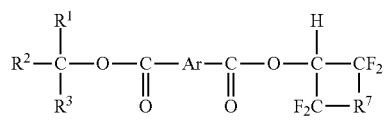

(2)

In the formula, Ar is a divalent aromatic hydrocarbon group or a divalent aromatic heterocyclic group; $R^1$ is a group represented by $CX^1Y^1R^4$; $R^2$ is a hydrogen atom or a group represented by $CX^2Y^2R^5$; $R^3$ is a hydrogen atom or a group represented by $CX^3Y^3R^6$; $R^7$ is a perfluoroalkylene group (which may contain an etheric oxygen) having 1 to 5 carbon atoms; $X^1$ to $X^3$ are each independently a hydrogen atom, a fluorine atom or $R^f$; $Y^1$ to $Y^3$ are each independently a fluorine atom or $R^f$; $R^4$ to $R^6$ are each independently a fluorine atom, $R^f$, $OR^f$ or an alkyl group having 1 to 6 carbon atoms; and $R^f$ is independently a fluoroalkyl group (which may contain an etheric oxygen) having 1 to 4 carbon atoms.

[Chem. 8]

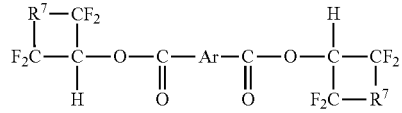

(3)

In the formula, Ar is a divalent aromatic hydrocarbon group or a divalent aromatic heterocyclic group; and $R^7$ is a perfluoroalkylene group (which may contain an etheric oxygen) having 1 to 5 carbon atoms, and two $R^7$s may be the same or different from each other.

Ar may be a group in which one or more hydrogen atoms are substituted with other substituents exerting no adverse influence on the reaction (for example, a halogen atom, an alkyl group having 1 to 10 carbon atoms, an alkoxy group having 1 to 10 carbon atoms, a phenyl group, a phenoxy group, a vinyl group, a cyano group, an ester group, an amido group, and a nitro group).

Specific examples of Ar include a phenylene group, a toluylene group, a xylylene group, a biphenylene group, a naphthylene group, a furylene group, a thienylene group, a pyrrolylene group and a pyridilene group. In view of heat resistance of the resulting polyester, a group of a 6 or more-membered ring is preferred, and in view of heat resistance of the resulting polyester and easy availability of a raw material, a group represented by the following formula (4) is more preferred.

[Chem. 9]

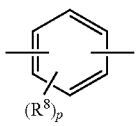

(4)

In the formula, p is an integer of 0 to 4; $R^8$ is a halogen atom, an alkyl group having 1 to 10 carbon atoms, an alkoxy group having 1 to 10 carbon atoms, a cycloalkyl group of a 5- to 10-membered ring, or a phenyl group; and when p is from 2 to 4, $R^8$s may be the same or different from each other.

Specific examples of the groups represented by formula (4) include 1,2-phenylene group, 1,3-phenylene group, 1,4-phenylene group, 3-methyl-1,2-phenylene group, 4-methyl-1,2-phenylene group, 2-methyl-1,3-phenylene group, 4-methyl-1,3-phenylene group, 5-methyl-1,3-phenylene group, 2-methyl-1,4-phenylene group, 3-phenyl-1,2-phenylene group, 4-phenyl-1,2-phenylene group, 2-phenyl-1,3-phenylene group, 4-phenyl-1,3-phenylene group, 5-phenyl-1,3-phenylene group, 2-phenyl-1,4-phenylene group, 3-t-butyl-1,2-phenylene group, 4-t-butyl-1,2-phenylene group, 2-t-butyl-1,3-phenylene group, 4-t-butyl-1,3-phenylene group, 5-t-butyl-1,3-phenylene group, 2-t-butyl-1,4-phenylene group, 3-cyclohexyl-1,2-phenylene group, 4-cyclohexyl-1,2-phenylene group, 2-cyclohexyl-1,3-phenylene group, 4-cyclohexyl-1,3-phenylene group, 5-cyclohexyl-1,3-phenylene group, and 2-cyclohexyl-1,4-phenylene group.

As the fluorine-containing dicarboxylic acid ester compounds, compound (1-1) and compound (1-2) are preferred in view of usefulness of the resulting polyester (polyarylate).

[Chem. 10]

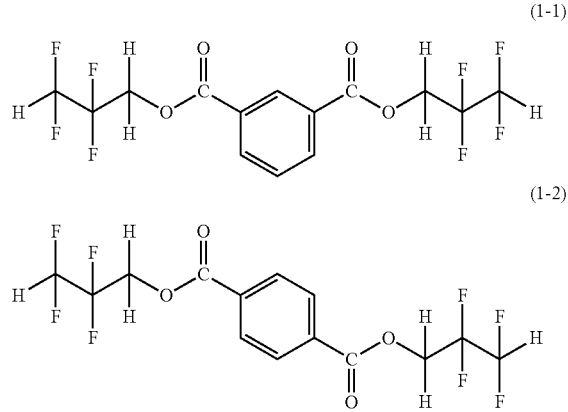

(Method for Producing Fluorine-Containing Dicarboxylic Acid Ester Compound)

The fluorine-containing dicarboxylic acid ester compound can be obtained by a reaction using as a starting material at least one fluorine-containing alcohol selected from the group consisting of compound (5) and compound (6):

[Chem. 11]

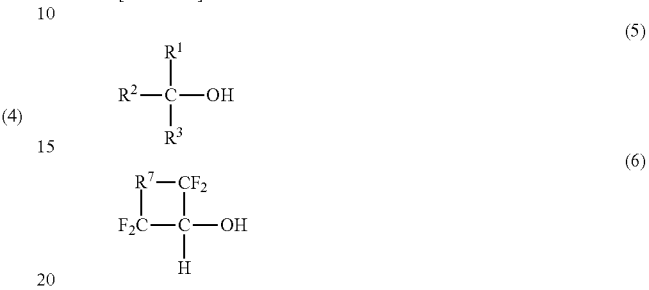

In the formula, $R^1$ is a group represented by $CX^1Y^1R^4$; $R^2$ is a hydrogen atom or a group represented by $CX^2Y^2R^5$; $R^3$ is a hydrogen atom or a group represented by $CX^3Y^3R^6$; $R^7$ is a perfluoroalkylene group (which may contain an etheric oxygen) having 1 to 5 carbon atoms; $X^1$ to $X^3$ are each independently a hydrogen atom, a fluorine atom or $R^f$; $Y^1$ to $Y^3$ are each independently a fluorine atom or $R^f$; $R^4$ to $R^6$ are each independently a fluorine atom, $R^f$, $OR^f$ or an alkyl group having 1 to 6 carbon atoms; and $R^f$ is independently a fluoroalkyl group (which may contain an etheric oxygen) having 1 to 4 carbon atoms.

As the fluorine-containing alcohol, an alcohol having a degree of acid dissociation higher than that of the diol compound is preferred in view of improving the transesterification reaction rate. Accordingly, preferred is a compound in which a fluoroalkyl group is directly bonded to an α-position carbon atom (hereinafter also referred to as a carbon) of a hydroxyl group. However, an alcohol in which a fluorine atom is directly bonded to an α carbon is unfavorable because a degradation reaction due to a dehydrofluorination reaction is liable to occur.

As a measure of the degree of acid dissociation, the pKa of the fluorine-containing alcohol is used. In the case where the diol compound is an aromatic diol compound, the pKa of the fluorine-containing alcohol is preferably less than 10 or nearly 10 because the pKa of phenols is about 10.

In the case where the diol compound is an aliphatic dial compound, the pKa of the fluorine-containing alcohol is preferably less than 15, and more preferably less than 13, because the pKa of aliphatic alcohols is about from 15 to 16.

Compound (5) is preferably a fluorine-containing alcohol in which $R^2$ is a group represented by $CX^2Y^2R^5$, namely a secondary or tertiary fluorine-containing alcohol, and more preferably a fluorine-containing alcohol in which $R^2$ and $R^3$ are a group represented by $CX^2Y^2R^5$ and a group represented by $CX^3Y^3R^6$, respectively, namely a tertiary fluorine-containing alcohol, because the more the fluoroalkyl groups bonded to α carbon are, the higher the degree of the acid dissociation of the fluorine-containing alcohol is.

The fluorine-containing alcohol preferably has 2 to 10 carbon atoms. If the fluorine-containing alcohol has 2 or more carbon atoms, a stable fluorine-containing alcohol in which no fluorine atom is directly bonded to the α position of a hydroxyl group can be selected. If the fluorine-containing alcohol has 10 or less carbon atoms, when the fluorine-containing alcohol dissociated at the time of the transesterification reaction is removed by distillation, the fluorine-containing alcohol has such a boiling point that it can be easily removed under mild conditions. Accordingly, it is unnecessary to apply high temperature at the time of the transesterification reaction, which makes it possible to produce the polyester having high quality.

Specific examples of the fluorine-containing alcohols include 2,2,2-trifluoroethanol (pKa: 12.4*[2]), 2,2,3,3,3-pentafluoro-1-propanol (pKa: 12.5*[2]), 2,2,3,3-tetrafluoro-1-propanol (pKa: 12.7*[3]), 1,1,1,3,3,3-hexafluoro-2-propanol (pKa: 9.4*[1]), 2-fluoro-1-propanol (pKa: 14.0*[3]), 2,2,3,4,4,4-hexafluoro-1-butanol (pKa: 12.5*[3]), 2,2,3,3,4,4,5,5-octafluoro-1-pentanol (pKa: 12.5*[3]), perfluoro(t-butyl) alcohol (pKa: 5.3*[1]), 2,2,3,3,4,4,5,5-octafluorocyclopentanol (pKa: 8.5*[1]) and 2,2,3,3,4,4,5,5,6,6-decafluorocyclohexanol (pKa: 8.5*[1]). Above all, 2,2,2-trifluoroethanol, 2,2,3,3,3-pentafluoro-1-propanol, 2,2,3,3-tetrafluoro-1-propanol and 1,1,1,3,3,3-hexafluoro-2-propanol are preferred in view of easy alcohol recovery at the polymerization temperature and industrially easy availability.

The pKa values (*1 to *3) of the fluorine-containing alcohols described above are values (*1) by the following measuring method, literature values (*2), and values (*3) by an estimation technique.

*1: The pKa of the fluorine-containing alcohol having a high degree of acid dissociation (strong acid strength) is determined based on the following:

The pKa is measured as the degree of acid dissociation of the fluorine-containing alcohol in an aqueous solution thereof.

HA(fluorine-containing alcohol)+S(water)→HS$^+$(conjugate acid of water)+A$^-$(conjugate base of fluorine-containing alcohol)

The formula of the equilibrium constant becomes the following equation.

Ka=[HS$^+$][A$^-$]/[HA][S]

When a dilute aqueous solution is assumed herein, [S] can be approximated by 1.

Ka=[HS$^+$][A$^-$]/[HA]

pKa=log [HA]/[HS$^+$][A$^-$]=−log [HS$^-$]−log [A$^-$]/[HA]

Since it is a degree of acid dissociation in the aqueous solution, −log [HS$^+$] is equal to the pH.

pKa=pH−log [A$^-$]/[HA]

In a half-neutralized state, [A$^-$]=[HA] holds, so that an approximation to pH=pKa can be made.

From the above-mentioned consideration, the pKa was measured with a potentiometric titrator, with respect to the fluorine-containing alcohols having high acidity.

*2: J. Amer. Chem. Soc., 96, 6851 (1974); J. Org. Chem., 32, 1217 (1967)

*3: Estimated values (estimated from the difference (Δλ) in stretching frequency between hydrogen-bonding OH and non-hydrogen-bonding OH based on the following literatures):

J. Org. Chem., 32, 1217 (1967); J. Amer. Chem. Soc., 86, 4948 (1964)

As a method for obtaining the fluorine-containing dicarboxylic acid ester compound by the reaction using a fluorine-containing alcohol as a starting material, the following methods (a) to (c) can be mentioned, and the method (c) is preferred in view of high yield.

(a) A method of obtaining the fluorine-containing dicarboxylic acid ester compound by transesterification reaction of compound (7) with a fluorine-containing alcohol in the presence of a catalyst:

[Chem. 12]

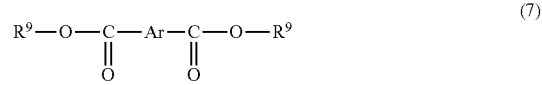
(7)

In the formula, Ar is a divalent aromatic hydrocarbon group or a divalent aromatic heterocyclic group; R$^9$ is an alkyl group or aryl group having 1 to 10 carbon atoms; and the alkyl group may be branched and may contain an etheric oxygen. Two R$^9$s may be the same or different from each other.

(b) A method of obtaining the fluorine-containing dicarboxylic acid ester compound by allowing compound (8) to react with a fluorine-containing alcohol in the presence of a catalyst:

[Chem. 13]

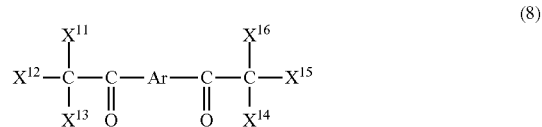
(8)

In the formula, Ar is a divalent aromatic hydrocarbon group or a divalent aromatic heterocyclic group; X$^{11}$ to X$^{13}$ are each independently a hydrogen atom or a halogen atom; at least one of X$^{11}$ to X$^{13}$ is a halogen atom; X$^{14}$ to X$^{16}$ are each independently a hydrogen atom or a halogen atom; and at least one of X$^{14}$ to X$^{16}$ is a halogen atom.

All of X$^{11}$ to X$^{16}$ are preferably halogen atoms, and more preferably fluorine atoms or chlorine atoms. It is most preferred that all are chlorine atoms because industrially useful chloroform can be produced together as a by-product.

(c) A method of obtaining the fluorine-containing dicarboxylic acid ester compound by allowing compound (9) to react with a fluorine-containing alcohol:

[Chem. 14]

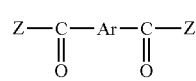
(9)

In the formula, Ar is a divalent aromatic hydrocarbon group or a divalent aromatic heterocyclic group; and Z is a halogen atom. Two Zs may be the same or different from each other.

As the catalysts used in the method (a), known transesterification reaction catalysts can be mentioned.

As the catalysts used in the method (b), there may be mentioned alkali metals and alkali earth metals; alkali metal hydrides and alkali earth metal hydrides; alkali metal hydroxides and alkali earth metal hydroxides; phase-transfer catalysts; alkali metal halides, alkali earth metal halides and ammonium halides; ion-exchange resins; compounds or oxides of at least one metal selected from the group consisting of Sn, Ti, Al, W, Mo, Zr and Zn; and transesterification reaction catalysts.

In the method (c), when Z is a fluorine atom or a chlorine atom, the reaction proceeds in an uncatalyzed state, and the desired product can be obtained by allowing the reaction to proceed while removing a hydrogen halide generated to the outside of the system by bubbling of an inert gas, heating or the like.

The ratio of the number of moles of the initially charged fluorine-containing alcohol to the number of moles of the initially charged compound (9) (fluorine-containing alcohol/compound (9)) in the method (c) is preferably more than 2, more preferably 2.5 or more, and particularly preferably 3 or more, in view of improved yield of the fluorine-containing dicarboxylic acid ester compound.

In the method (c), for the purpose of adjusting the viscosity of the reaction system or adjusting the amount of heat generation, a solvent may be used. However, in view of the volumetric efficiency of a reactor and the loss of the desired product in a solvent separation process, it is preferred that the reaction is performed in a solvent-free state, if possible.

The reaction temperature in the method (c) is preferably from 40 to 200° C.

The reaction pressure in the method (c) is usually the atmospheric pressure.

(Diol Compounds)

As the dial compounds, aliphatic diol compounds and aromatic diol compounds are mentioned. The aromatic dial compounds are preferred because the industrially useful polyarylate is obtained.

As the aliphatic dial compound, an aliphatic diol compound having 2 to 12 carbon atoms is preferably, in view of heat resistance, chemical resistance and mechanical properties of the polyester.

Specific examples of the aliphatic diol compounds include ethylene glycol, diethylene glycol, triethylene glycol, tetraethylene glycol, 3-chloro-1,2-propanediol, 2-chloro-1,3-propanediol, cyclohexanediol, 1,2-propylene glycol, dipropylene glycol, tripropylene glycol, 1,3-propanediol, 1,2-butanediol, 1,3-butanediol, 1,4-butanediol, 1,4-butenediol, 2-methyl-2,4-pentanediol (hexylene glycol), 3-methyl-1,5-pentanediol, 1,5-pentanediol, 1,6-hexanediol and fluorine-containing diols (such as 3,3,3-trifluoro-1,2-propanediol).

As the aromatic diol compound, an aromatic diol compound having 6 to 20 carbon atoms is preferably, in view of heat resistance, chemical resistance, mechanical properties and moldability of the polyester (polyarylate).

Specific examples of the aromatic diol compounds include resorcinol, catechol, hydroquinone, 2,2-(bis(4-hydroxyphenyl)propane [alternative name: bisphenol A], 2,2-bis(4-hydroxyphenyl)hexafluoropropane [alternative name: bisphenol AF], bis(4-hydroxyphenyl)methane, 4,4'-dihydroxybiphenyl, bis(4-hydroxybiphenyl)ether, dihydroxynaphthalene, phloroglucinol and condensates of phenols. In view of easy availability of a raw material and usefulness of the polyarylate, bisphenol A is preferred.

(Transesterification Reaction)

As a specific method for obtaining a polyester by transesterifying the fluorine-containing dicarboxylic acid ester compound with a diol compound in the presence of a catalyst, the following methods (A) and (B) can be mentioned, and the method (A) is preferred because the polyester can be produced by a simple process.

(A) A method of subjecting the fluorine-containing dicarboxylic acid ester compound and a diol compound to melt polycondensation in the presence of a catalyst; and (B) A method of subjecting the fluorine-containing dicarboxylic acid ester compound and a diol compound to solution polycondensation in the presence of the catalyst.

The reaction temperature in the method (A) is preferably equal to or higher than the melting point of the diol compound or the fluorine-containing dicarboxylic acid ester compound in an early stage of the reaction, and preferably equal to or higher than the melting point of the polyester in a later stage of the reaction. Further, the reaction temperature in the method (A) is preferably 300° C. or less, in view of inhibited coloration of the polyester.

The ratio of the number of moles of the initially charged fluorine-containing dicarboxylic acid ester compound to the number of moles of the initially charged diol compound (fluorine-containing dicarboxylic acid ester compound/diol compound) may be appropriately selected depending on the desired molecular weight of the polyester.

The fluorine-containing dicarboxylic acid ester compound/diol compound ratio (molar ratio) is preferably from 0.95 to 1.20 because the polyester having a molecular weigh of about 1,000 to about 100,000 is obtained.

(Function and Effect)

In the production method of a polyester of the present invention described above, the specific fluorine-containing dicarboxylic acid ester compound derived from the fluorine-containing alcohol which has a relatively high degree of acid dissociation and a low boiling point compared to that of phenols as aromatic hydrocarbon and can be easily removed to the outside of the system is transesterified with a diol compound, so that the polymerization reaction rate is high, which makes polymerization possible at low temperature. Further, it is unnecessary to use a solvent. Accordingly, the polyester having little coloration, a high purity and a high molecular weight can be produced by the simple process.

That is to say, in the fluorine-containing dicarboxylic acid ester compound in the present invention, the degree of dissociation of an ester site is high due to the effect of electron withdrawing properties caused by the fluorine atom, so that the transesterification reaction thereof with an aromatic diol compound or aliphatic diol compound is easily performed. Further, the rate of transesterification reaction as an equilibrium reaction can be accelerated because the alcohol obtained as a by-product has a low boiling point and therefore can be rapidly removed to the outside of the polymerization system by distillation. Accordingly, the production method of a polyester of the present invention using the fluorine-containing dicarboxylic acid ester compound can solve the problems of difficulty of obtaining a high-molecular-weight polymer, coloration due to the reaction at high temperature for a long period of time, and the like, which are problems in the production method of a polyester using the conventional transesterification.

EXAMPLES

The present invention will be described below in more detail with reference to examples, but the present invention is not construed as being limited to these examples.

(Gas Chromatography (GC) Analysis)

GC analysis was performed using the following apparatus under the following conditions:

Apparatus: GC-17A, manufactured by Shimadzu Corporation

Detection method: FID detection (Gas Chromatography Mass (GC-Mass) Analysis)

GC-Mass analysis was performed using the following apparatus under the following conditions:

Apparatus: GC-17A/QP-5050A system, manufactured by Shimadzu Corporation

Detection method: EI detection (NMR Analysis)

NMR analysis was performed using the following apparatus under the following conditions:
 Apparatus: AL300, manufactured by JEOL Ltd.
 $^1$H-NMR (300.4 MHz, solvent: CDCl$_3$, reference: TMS)
 $^{19}$F-NMR (282.65 MHz, solvent: CDCl$_3$, reference: CFCl$_3$)

(Gel Permeation Chromatography (GPC) Analysis)

The molecular weight of the polyester synthesized was determined by performing analysis using the following apparatus under the following conditions and converted to that of polystyrene as a standard substance.
 Apparatus: HLC-8220GPC, manufactured by Tosoh Corporation
 Guard column: TSK guardcolumn Super MPHZ-M
 Column: TSKgel SuperMultipore HZ-M, 3 columns
 Mobile phase: tetrahydrofuran
 Flow rate: 0.35 mL/min
 Detection method: RI detection
 Column temperature: 40° C.

Synthesis Example 1

Synthesis of Bis(2,2,3,3-tetrafluoropropyl) Isophthalate (Compound (1-1))

Into a 2000-mL glass reactor equipped with a thermometer, a stirrer, a reflux condenser, and a dropping funnel, 500 g (2.46 mol) of isophthaloyl chloride (compound (9-1)) was charged, and thereafter, the temperature thereof was increased to 100° C. with stirring. Then, 715.53 g (5.41 mol) of 2,2,3,3-tetrafluoropropanol (compound (5-1)) was added dropwise thereto with adjustment of the dropping rate while observing an increase (ΔT) of the internal temperature and the degree of hydrogen chloride gas generation. After the dropping was completed, stirring was performed at 100° C. for 1 hour. Thereafter, the temperature thereof was increased to 140° C. while observing the degree of hydrogen chloride gas generation, and heating was performed for 9 hours in total. After the reaction was completed, the crude solution was cooled to room temperature. Thereafter, a part of the crude solution was collected and subjected to $^1$H-NMR analysis. As a result, it was confirmed that compound (1-1) was produced as a main product (yield based on compound (5-1): 41.8%). Compound (1-1) as the product was obtained in a yield of 93.5%.

[Chem. 15]

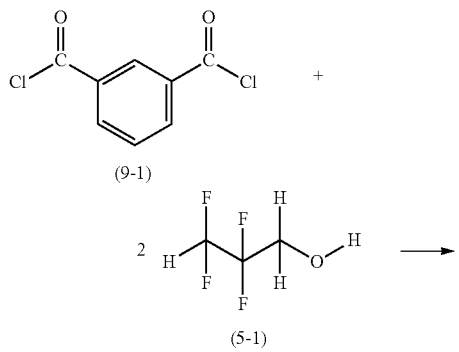

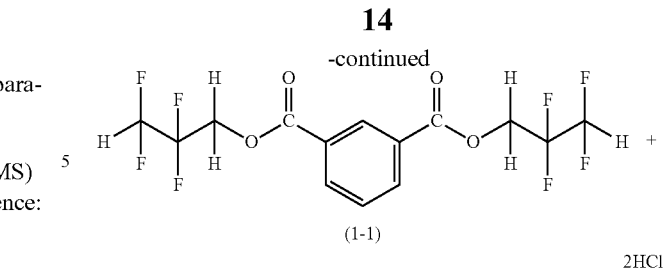

For compound (1-1) as the product, structure assignments were performed by $^{19}$F-NMR analysis and GC-Mass analysis, in addition to $^1$H-NMR analysis. The results of $^1$H-NMR, $^{19}$F-NMR and mass fragments of compound (1-1) are shown below.

$^1$H-NMR δ: 4.762 (4H, t, J=12.6 Hz), 5.962 (2H, tt, J=3.3, 52.9 Hz), 7.617 (1H, t, J=7.8 Hz), 8.297 (2H, dd, J=1.8, 7.8 Hz), 8.711 (1H, t, J=1.5 Hz)

$^{19}$F-NMR δ: −137.142 (4F, d, 53.1 Hz), −123.257 (4F, tdt, J=1.7, 3.3, 12.2 Hz)

MS ink: 235 (PhC(=O)OCH$_2$CF$_2$CF$_2$H); 263 (C(O)PhC(=O)OCH$_2$CF$_2$CF$_2$H); 343 (CF$_2$CH$_2$OC(=O)PhC(=O)OCH$_2$CF$_2$CF$_2$H); 394 (CF$_2$HCF$_2$CH$_2$C(=O)PhC(=O)OCH$_2$CF$_2$CF$_2$H)

Synthesis Example 2

Synthesis of Bis(2,2,3,3-tetrafluoropropyl)Terephthalate (Compound (1-2))

Into a 3000-mL glass reactor equipped with a stirrer, a reflux condenser and a dropping funnel, 857.21 g (4.22 mol) of terephthaloyl chloride (compound (9-2)) was charged, and thereafter, the temperature thereof was increased to 100° C. with stirring. Then, 1248.84 g (9.46 mol) of 2,2,3,3-tetrafluoropropanol (compound (5-1)) was added dropwise thereto with adjustment of the dropping rate while observing an increase (ΔT) of the internal temperature and the degree of hydrogen chloride gas generation. After the dropping was completed, stirring was performed at 100° C. for 1 hour. Thereafter, the temperature thereof was increased to 140° C. while observing the degree of hydrogen chloride gas generation, and heating was performed for 9 hours in total. After the reaction was completed, the crude solution was cooled to room temperature. Thereafter, a part of the crude solution was collected and subjected to $^1$H-NMR analysis. As a result, it was confirmed that compound (1-2) was produced as a main product (yield based on compound (5-1): 43.1%). Compound (1-2) as the product was obtained in a yield of 96.7%.

[Chem. 16]

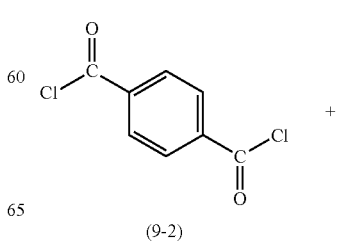

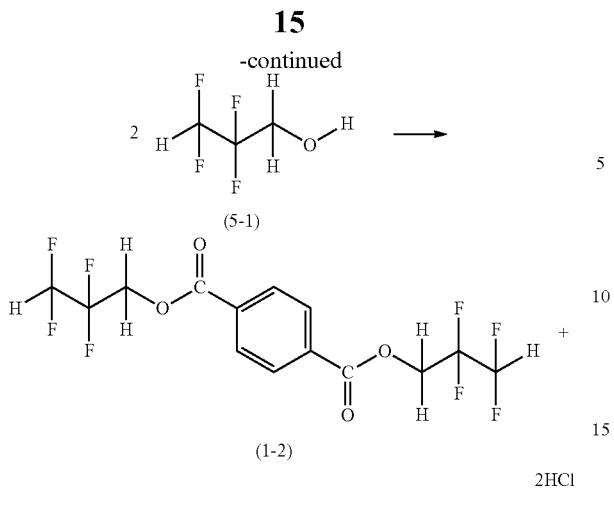

For compound (1-2) as the product, structure assignments were performed by $^{19}$F-NMR analysis and GC-Mass analysis, in addition to $^1$H-NMR analysis. The results of $^1$H-NMR, $^{19}$F-NMR and mass fragments of compound (1-2) are shown below.

$^1$H-NMR δ: 4.760 (4H, tt, J=1.2, 12.9 Hz), 5.947 (2H, tt, J=3.3, 53.2 Hz), 8.154 (4H, s)

$^{19}$F-NMR δ: −137.020 (4F, d, 52.9 Hz), −123.203 (4F, tdt, J=13.0, 3.4, 1.7 Hz)

MS m/z: 235 (PhC(=O)OCH$_2$CF$_2$CF$_2$H); 263 (C(=O)PhC(=O)OCH$_2$CF$_2$CFH); 343 (CF$_2$CH$_2$OC(=O)PhC(=O)OCH$_2$CF$_2$CF$_2$H); 394 (CF$_2$HCF$_2$CH$_2$OC(=O)PhC(=O)O CH$_2$CF$_2$CF$_2$H)

Example 1

Synthesis 1 of Polyarylate

Into a 300-mL reactor of a melt polymerization apparatus, 20.99 g (0.092 mol) of bisphenol A (compound (10)), 27.20 g (0.069 mol) of compound (1-1), 9.07 g (0.023 mol) of compound (1-2), and 0.0027 g (0.5×10$^{-4}$ mol) of potassium borohydride were charged. The following deoxygenation process was repeated three times.

Deoxygenation process: The reactor was evacuated at 0° C. until the pressure therein reached about 1 Torr, thereby removing oxygen, and thereafter, the reactor was filled again with nitrogen to the atmospheric pressure.

[Chem. 17]

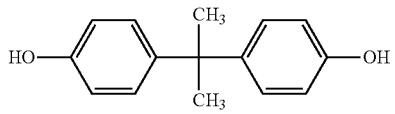

(10)

The reactor was immersed in an oil bath preheated to 200° C. Stirring was performed at an oil bath temperature of 200° C. and a stirring speed of 200 rpm. As a result, thermal equilibration was achieved after 10 minutes, and the solid matters were completely melted to form a colorless uniform liquid. Thereafter, at the time when the reaction was continued for 5 minutes while maintaining the pressure in the reactor at 740 Torr and the temperature in the reactor at 230° C., compound (5-1) was exhausted from the reactor and started to be distilled out in a receiving flask. After 60 minutes, the temperature in the reactor was increased to 250° C., and the pressure in the reactor was maintained at 300 Torr. After 60 minutes, the temperature in the reactor was increased to 270° C., and the pressure in the reactor was maintained at 10 Torr. After 60 minutes, the temperature in the reactor was increased to 280° C., and the pressure in the reactor was maintained at 1 Torr. After 30 minutes, the polymerization was terminated by cooling to room temperature to obtain a polyarylate represented by the following formula (11):

[Chem. 18]

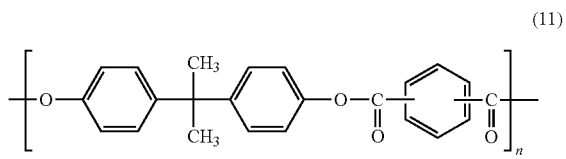

(11)

The mass average molecular weight (Mw) of the resulting polyarylate measured by GPC analysis was 13,962, the number average molecular weight (Mn) thereof was 9,215, and the degree of dispersion (Mw/Mn) was 1.515. The polyarylate had no coloration and was recognized as a high purity one. The results thereof are shown in Table 1.

Comparative Example 1

Synthesis 2 of Polyarylate

Into a 300-mL reactor of a melt polymerization apparatus, 20.99 g (0.092 mol) of bisphenol A (compound (10)), 21.96 g (0.069 mol) of diphenyl isophthalate, 7.32 g (0.023 mol) of diphenyl terephthalate, and 0.0027 g (0.5×10$^{-4}$ mol) of potassium borohydride were charged. The following deoxygenation process was repeated three times.

Deoxygenation process: The reactor was evacuated at 0° C. until the pressure therein reached about 1 Torr, thereby removing oxygen, and thereafter, the reactor was filled again with nitrogen to the atmospheric pressure.

The reactor was immersed in an oil bath preheated to 200° C. Stirring was performed at an oil bath temperature of 200° C. and a stirring speed of 200 rpm. As a result, thermal equilibration was achieved after 10 minutes, and the solid matters were completely melted to form a colorless uniform liquid. Thereafter, at the time when the reaction was continued for 5 minutes while maintaining the pressure in the reactor at 260 Torr and the temperature in the reactor at 250° C., phenol was exhausted from the reactor and started to be distilled out in a receiving flask. After 60 minutes, the temperature in the reactor was increased to 270° C., and the pressure in the reactor was maintained at 150 Torr. After 60 minutes, the temperature in the reactor was increased to 290° C., and the pressure in the reactor was maintained at 10 Torr. After 60 minutes, the temperature in the reactor was increased to 300° C., and the pressure in the reactor was maintained at 1 Torr. After 30 minutes, the polymerization was terminated by cooling to room temperature to obtain a polyarylate.

The mass average molecular weight (Mw) of the resulting polyarylate measured by GPC analysis was 12,091, the number average molecular weight (Mn) thereof was 7,312, and the degree of dispersion (Mw/Mn) was 1.654. The polyarylate had no coloration and was recognized as a high purity one. The results thereof are shown in Table 1.

TABLE 1

| | Example 1 | Comparative Example 1 |
|---|---|---|
| Diol Compound | Bisphenol A: 20.99 g | Bisphenol A: 20.99 g |
| Dicarboxylic Acid Ester | Bis(2,2,3,3-tetrafluoropropyl) isophthalate: 27.2 g<br>Bis(2,2,3,3-tetrafluoropropyl) terephthalate: 9.07 g | Diphenyl isophthalate: 21.96 g<br>Diphenyl terephthalate: 7.32 g |
| Catalyst | potassium borohydride: 0.0027 g | potassium borohydride: 0.0027 g |
| Temperature, Pressure, Time | (1) 230° C., 740 Torr, 60 min<br>(2) 250° C., 300 Torr, 60 min<br>(3) 270° C., 10 Torr, 60 min<br>(4) 280° C., 1 Torr, 30 min | (1) 250° C., 260 Torr, 60 min<br>(2) 270° C., 150 Torr, 60 min<br>(3) 290° C., 10 Torr, 60 min<br>(4) 300° C., 1 Torr, 30 min |
| Mw | 13,962 | 12,091 |
| Mn | 9,215 | 7,312 |
| Mw/Mn | 1.515 | 1.654 |
| Polymer Color | Colorless and transparent | Colorless and transparent |

In Example 1 using the fluorine-containing dicarboxylic acid ester compounds, the polyarylate having a higher molecular weight could be synthesized at a lower polymerization temperature, compared to Comparative Example 1 using diphenyl phthalates usually used in the conventional melt methods.

While the invention has been described in detail and with reference to specific embodiments thereof, it will be apparent to one skilled in the art that various changes and modifications can be made therein without departing from the spirit and scope of the invention.

This application is based on Japanese Patent Application No. 2011-045195 filed on Mar. 2, 2011, and the contents of which are incorporated herein by way of reference.

INDUSTRIAL APPLICABILITY

The polyesters obtained by the production method of the present invention are useful as materials for fibers, films, containers and the like, and particularly, the polyarylates are useful as engineering plastics.

The invention claimed is:

1. A method for producing a polyester, comprising conducting a transesterification reaction of at least one compound selected from the group consisting of a compound represented by the following formula (1), a compound represented by the following formula (2) and a compound represented by the following formula (3) with a diol compound in the presence of a catalyst:

[Chem. 1]

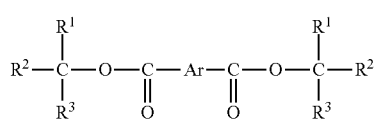

(1)

wherein Ar is a divalent aromatic hydrocarbon group or a divalent aromatic heterocyclic group,
$R^1$ is a group represented by $CX^1Y^1R^4$, and two $R^1$s may be the same or different from each other,
$R^2$ is a hydrogen atom or a group represented by $CX^2Y^2R^5$, and two $R^2$s may be the same or different from each other,
$R^3$ is a hydrogen atom or a group represented by $CX^3Y^3R^6$, and two $R^3$s may be the same or different from each other,
$X^1$ to $X^3$ are each independently a hydrogen atom, a fluorine atom or $R^f$,
$Y^1$ to $Y^3$ are each independently a fluorine atom or $R^f$,
$R^4$ to $R^6$ are each independently a fluorine atom, $R^f$, $OR^f$ or an alkyl group having 1 to 6 carbon atoms, and
$R^f$ is independently a fluoroalkyl group (which may contain an etheric oxygen) having 1 to 4 carbon atoms;

[Chem. 2]

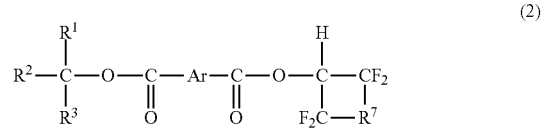

(2)

wherein Ar is a divalent aromatic hydrocarbon group or a divalent aromatic heterocyclic group,
$R^1$ is a group represented by $CX^1Y^1R^4$,
$R^2$ is a hydrogen atom or a group represented by $CX^2Y^2R^5$,
$R^3$ is a hydrogen atom or a group represented by $CX^3Y^3R^6$,
$R^7$ is a perfluoroalkylene group (which may contain an etheric oxygen) having 1 to 5 carbon atoms,
$X^1$ to $X^3$ are each independently a hydrogen atom, a fluorine atom or $R^f$,
$Y^1$ to $Y^3$ are each independently a fluorine atom or $R^f$,
$R^4$ to $R^6$ are each independently a fluorine atom, $R^f$, $OR^f$ or an alkyl group having 1 to 6 carbon atoms, and
$R^f$ is independently a fluoroalkyl group (which may contain an etheric oxygen) having 1 to 4 carbon atoms; and

[Chem. 3]

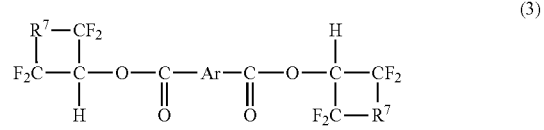

(3)

wherein Ar is a divalent aromatic hydrocarbon group or a divalent aromatic heterocyclic group, and
$R^7$ is a perfluoroalkylene group (which may contain an etheric oxygen) having 1 to 5 carbon atoms, and two $R^7$s may be the same or different from each other.

2. The method for producing a polyester according to claim 1, wherein the compound represented by the above formula (1) to (3) is obtained by a reaction using as a starting material at least one fluorine-containing alcohol selected from the group consisting of a compound represented by the following formula (5) and a compound represented by the following formula (6):

[Chem. 4]

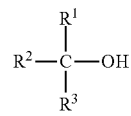

(5)

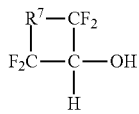

(6)

wherein $R^1$ is a group represented by $CX^1Y^1R^4$,
$R^2$ is a hydrogen atom or a group represented by $CX^2Y^2R^5$,
$R^3$ is a hydrogen atom or a group represented by $CX^3Y^3R^6$,
$R^7$ is a perfluoroalkylene group (which may contain an etheric oxygen) having 1 to 5 carbon atoms,
$X^1$ to $X^3$ are each independently a hydrogen atom, a fluorine atom or $R^f$,
$Y^1$ to $Y^3$ are each independently a fluorine atom or $R^f$,
$R^4$ to $R^6$ are each independently a fluorine atom, $R^f$, $OR^f$ or an alkyl group having 1 to 6 carbon atoms, and
$R^f$ is independently a fluoroalkyl group (which may contain an etheric oxygen) having 1 to 4 carbon atoms.

3. The method for producing a polyester according to claim 2, wherein the fluorine-containing alcohol has 2 to 10 carbon atoms.

4. The method for producing a polyester according to claim 2, wherein $R^2$ in formula (5) is a group represented by $CX^2Y^2R^5$.

5. The method for producing a polyester according to claim 2, wherein the fluorine-containing alcohol has a pKa of less than 15.

6. The method for producing a polyester according to claim 2, wherein the fluorine-containing alcohol has a pKa of less than 13.

7. The method for producing a polyester according to claim 2, wherein the fluorine-containing alcohol is at least one selected from the group consisting of 2,2,2-trifluoroethanol, 2,2,3,3-tetrafluoro-1-propanol, 2,2,3,3,3-pentafluoro-1-propanol, 1,1,1,3,3,3-hexafluoro-2-propanol, 2-fluoro-1-propanol, 2,2,3,4,4,4-hexafluoro-1-butanol, 2,2,3,3,4,4,5,5-octafluoro-1-pentanol, 2,2,3,3,4,4,5,5-octafluorocyclopentanol, perfluoro(t-butyl) alcohol, and 2,2,3,3,4,4,5,5,6,6-decafluorocyclohexanol.

8. The method for producing a polyester according to claim 1, wherein the diol compound is an aromatic diol compound.

9. The method for producing a polyester according to claim 1, wherein the diol compound is bisphenol A.

10. The method for producing a polyester according to claim 1, wherein the catalyst is an alkali metal salt or an alkali earth metal salt.

11. Bis(2,2,3,3-tetrafluoropropyl)isophthalate represented by the following formula (1-1):

[Chem. 5]

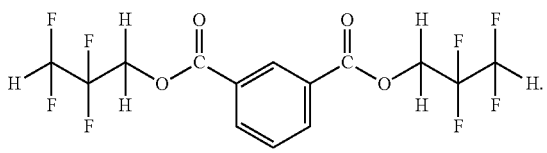

(1-1)

* * * * *